United States Patent [19]

Försch et al.

[11] 4,277,470

[45] Jul. 7, 1981

[54] HETEROCYCLIC SPIRO-LINKED AMIDINES, COMPOSITIONS AND USE THEREOF

[75] Inventors: Manfred Försch, Nauheim; Wolfgang Schaub, Kelkheim; Hermann Gerhards, Hofheim am Taunus, all of Fed. Rep. of Germany

[73] Assignee: Hoechst Aktiengesellschaft, Frankfurt am Main, Fed. Rep. of Germany

[21] Appl. No.: 123,200

[22] Filed: Feb. 21, 1980

[30] Foreign Application Priority Data

Feb. 23, 1979 [DE] Fed. Rep. of Germany ....... 2907070

[51] Int. Cl.³ .................... A61K 31/40; A61K 31/54; C07D 207/22; C07D 295/00
[52] U.S. Cl. ............................. 424/246; 424/248.4; 424/248.55; 424/248.58; 424/250; 424/267; 424/274; 544/6; 544/70; 544/230; 546/15; 546/20; 260/245.7; 260/326.25; 260/326.38; 260/326.5 D; 260/326.5 L; 260/326.62; 260/326.8; 260/326.84; 260/326.85; 260/326.82; 260/326.9
[58] Field of Search ............... 544/6, 70, 230; 546/15, 546/20; 260/245.7, 326.38, 326.5 D, 326.5 L, 326.82, 326.8, 326.25, 326.62, 326.84, 326.85, 326.9; 424/246, 248.55, 248.58, 248.4, 250, 267, 274

[56] References Cited

U.S. PATENT DOCUMENTS 2,931,805   4/1960   Weinstock ................. 260/326.5 FL Primary Examiner—Henry R. Jiles
Assistant Examiner—R. W. Ramsuer
Attorney, Agent, or Firm—Curtis, Morris & Safford

[57] ABSTRACT

Heterocyclic, spiro-linked amidines of the formula I

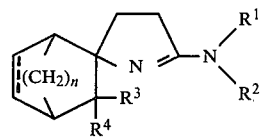

and their physiologically acceptable salts, in which (a) n is 1 or 2; (b) $R^1$ and $R^2$ are hydrogen or alkyl radicals which, together with the nitrogen atom, can form a 5-, 6- or 7-membered ring which can be substituted by $C_1$–$C_3$-alkyl, $C_1$–$C_2$-alkoxy, hydroxyl or $C_1$–$C_4$-alkoxycarbonyl groups and in which one of the carbon atoms can also be replaced by an oxygen, sulfur or nitrogen atom, it being possible for the nitrogen atom to be substituted by hydrogen, by the formyl group or by a phenyl radical, which can in turn be monosubstituted or polysubstituted by a $C_1$ to $C_4$-alkyl group or an alkoxy, methylenedioxy, hydroxyl, halogen, nitro or amino group, or it being possible for the nitrogen atom to be substituted by a $C_1$–$C_4$-alkyl group, or in which $R^1$ represents hydrogen and $R^2$ represents a $C_5$–$C_8$-cycloalkyl radical which can be substituted by $C_1$–$C_4$-dialkylamino groups; (c) $R^3$ is hydrogen or methyl and (d) $R^4$ denotes a phenyl radical which is optionally monosubstituted or polysubstituted by $C_1$–$C_4$-alkyl, $C_1$–$C_4$-alkoxy, methylenedioxy, hydroxyl, halogen, cyano, nitro, trifluoromethyl, amino, $C_2$–$C_5$-acylamino or mono- or di-$C_1$–$C_4$-alkylamino groups, or a thiophene radical, their stereoisomers and optical isomers, processes for their preparation and antidepressive medicaments containing these compounds.

10 Claims, No Drawings

HETEROCYCLIC SPIRO-LINKED AMIDINES, COMPOSITIONS AND USE THEREOF

The invention relates to a new class of heterocyclic spiro-linked amidines which have a powerful antidepressant action, processes for the preparation of these new compounds, new intermediate products which are suitable for the preparation of the active compounds according to the invention, and pharmaceutical agents which contain the active compounds according to the invention and the use thereof as medicaments for the treatment of depressive conditions.

The invention relates to heterocyclic, spiro-linked amidines of the formula I

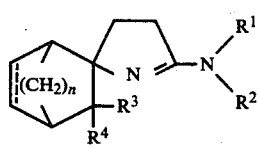

in which n is 1 or 2; $R^1$ and $R^2$ denote hydrogen or alkyl radicals, which, together with the nitrogen, can form a 5-, 6- or 7-membered ring which can be substituted by $C_1$-$C_3$-alkyl, $C_1$-$C_2$-alkoxy, hydroxyl or $C_1$-$C_4$-alkoxycarbonyl groups and in which one of the carbon atoms can also be replaced by an oxygen, sulfur or nitrogen atom, it being possible for the nitrogen atom to be substituted by hydrogen, the formyl group or a phenyl radical, which can in turn be monosubstituted or polysubstituted by a $C_1$-$C_4$-alkyl group or an alkoxy, methylenedioxy, hydroxyl, halogen, nitro or amino group, or it being possible for the nitrogen atom to be substituted by a $C_1$-$C_4$-alkyl group, or in which $R^1$ represents hydrogen and $R^2$ represents a $C_5$-$C_8$-cycloalkyl radical which can be substituted by $C_1$-$C_4$-dialkylamino groups; $R^3$ is hydrogen or methyl and $R^4$ denotes a phenyl radical which is optionally monosubstituted or polysubstituted by $C_1$-$C_4$-alkyl, $C_1$-$C_4$-alkoxy, methylenedioxy, hydroxyl, halogen, cyano, nitro, trifluoromethyl, amino, $C_2$-$C_5$-acylamino or mono- or di-$C_1$-$C_4$-alkylamino groups, or a thiophene radical; and the physiologically acceptable salts of compounds of the formula I.

The invention also relates to the compounds used as intermediate products, of the formula II

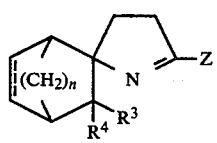

in which n, $R^3$ and $R^4$ have the meanings given for formula I and Z denotes a halogen atom or a SH, $SR^5$ or $OR^5$ radical, in which $R^5$ represents a $C_1$-$C_6$-alkyl, benzyl, phenylalkyl or phenylsulfonyl radical.

The compounds of the formula I according to the invention can be prepared by (a) reacting a compound of the formula III

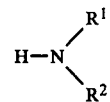

in which n, $R^3$ and $R^4$ have the meanings given for formula I, with phosphorus oxychloride or phosphorus pentoxide and an amine of the formula IV

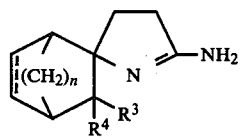

in which $R^1$ and $R^2$ have the meaning given for formula I; or (b) reacting a compound of the formula II with an amine of the formula IV; or (c) reacting a compound of the formula V

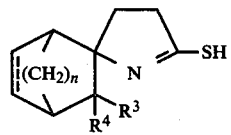

in which n, $R_3$ and $R_4$ have the meanings given for formula I, with an alkylating agent; or (d) reacting a compound of the formula III with an arylsulfonyl chloride in dry pyridine at a temperature of $-30°$ C. to room temperature, preferably at $-10°$ C., to give the intermediate imino-ester, which reacts further with the amine component of the formula IV.

The compounds of the formula II used as intermediate products are prepared (a') if Z is halogen, by reacting a compound of the formula III with an inorganic acid halide;

(b') if Z is $SR^5$, by reacting a compound of the formula VI

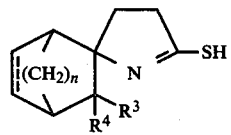

in which n, $R_3$ and $R_4$ have the meanings given for formula I, with an alkylating agent;

(c') if Z is $OR^5$, by reacting a compound of the formula III with a trialkyloxonium fluoborate $R_3^5$ $OBF_4$; or (d') if Z is $OR^5$, by reacting a compound of the formula III with an acid halide and then treating the product in situ with an alkali metal alcoholate; or (e') if Z is SH, by reacting a compound of the formula III with phosphorus pentasulfide or the phosphorus pentasulfide-pyridine complex.

The preparation of the compounds of the formula I according to the invention by process a is carried out at a temperature of $0°$-$120°$ C., preferably at $50°$ C., in an inert solvent, preferably benzene, toluene, chloroform, carbon tetrachloride, trichloroethylene or dioxan.

In process b, a compound of the formula II is dissolved in an inert solvent, preferably diethylene glycol dimethyl ether, dioxan, dimethylformamide or tetrahydrofuran, and either the gaseous amine is passed into this solution or the liquid or dissolved amine is added to the solution. Depending on the starting substance II employed, the reaction is carried out either with cooling, or at room temperature, or at moderately elevated temperatures.

Compounds of the formula II in which Z denotes a halogen atom, preferably Cl or Br, can be reacted with the amine directly, without prior isolation, in the reaction solution containing the imide halide.

Compounds of the general formula II in which Z represents a $SR^5$ radical are reacted with an amine of the formula IV in a protic solvent, preferably an alcohol, such as methanol or isopropanol. It can also be advantageous to use dimethylformamide. In the case of high-boiling amine derivatives of the formula IV, the reaction can be carried out without a solvent at the boiling point of the amine, but preferably not above 140° C.

In process c, a compound of the formula V is reacted with an alkylating agent, for example an alkyl halide or an alkyl sulfate or dialkyl sulfate, by customary and known methods, or is reacted by other customary processes, for example in accordance with the method of Leuchart-Wallach.

The reaction in process d is preferably carried out in dry pyridine at a temperature of −30° C. to 20° C., preferably at −10° C. (H. Henecka, P. Kurtz, Houben-Weyl, Methoden der organischen Chemie, Sauerstoffverbindungen III (Methods of Organic Chemistry, Oxygen Compounds III), Volume 8, page 704 (1952)).

The compounds of the formula II used as intermediate products are obtained as follows:

In process a', preferably, phosphorus pentahalides are reacted with compounds of the formula III in an anhydrous inert organic solvent, such as dioxan, chloroform, carbon tetrachloride or trichloroethylene, at temperatures of −40° C. to 50° C., preferably at −10° C.

In process b', suitable alkylating agents are alkyl halides, preferably methyl iodide and ethyl bromide, and furthermore diesters of sulfuric acid or of toluenesulfonic acid. Alcohols, such as methanol, or tetrahydrofuran or dioxan are preferably used as the solvent, and acetone is particularly preferably suitable. The reaction temperature is between 0° C. and the boiling point of the solvent chosen, and is preferably 30°-60° C.

The triethyloxonium fluoborate, obtainable from boron trifluoride-etherate and epichlorohydrin (compare H. Meerwein et al., J.pr. Chem.(2), 147 257 (1937); and 154, 83 (1939)), used in process c' is reacted in situ with a compound of the formula III. Diethyl ether or halogenated hydrocarbons, for example carbon tetrachloride, are particularly suitable solvents. The reaction temperature is between 0° C. and the boiling point of the solvent used, and is preferably 30°-40° C.

In process d', the imide halide of the formula II in which Z=halogen, which is obtainable in an inert solvent by process a', is reacted in situ with an alkali metal alcoholate, preferably sodium methylate or ethylate. The reaction temperature is 0° C.-60° C., preferably 30°-40° C.

The reaction of compounds of the formula III with phosphorus pentasulfide by process e' is carried out in a suitable solvent, such as, for example, pyridine or toluene, and with calcium oxide as a basic catalyst, at 20°-120° C., preferably at 50° C. However, it is also possible to react compounds of the formula III with the commercially available phosphorus pentasulfide-pyridine complex compound in an inert solvent, such as benzene, chloroform, methylene chloride, tetrahydrofuran or dioxan, but preferably in pyridine or toluene, at 30°-110° C., preferably at 60°-80° C.

The starting substances of the formula IX in which $R^3$ is hydrogen or methyl and $R^4$ is phenyl, methoxyphenyl, hydroxyphenyl, chlorophenyl or aminophenyl are described in U.S. Pat. No. 2,931,805. Compounds of the formula IX with other substituents for $R^4$ can be prepared in a corresponding manner, by the following reaction:

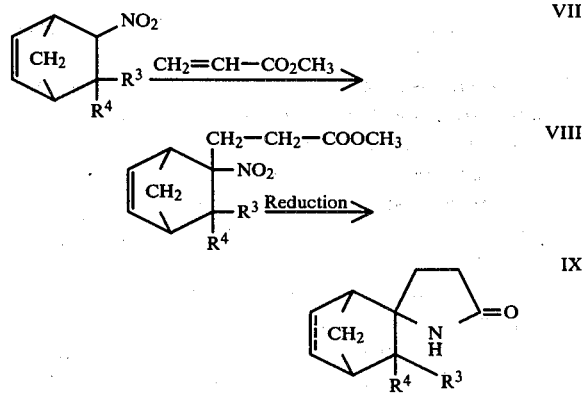

The nitro-bicyclic compounds of the formula VII in which $R^3$ and $R^4$ have the meaning given for formula I can be prepared by a Diels-Alder reaction from corresponding ω-nitrostyrenes in boiling cyclopentadiene (Literature: J.Org. Chem. 26, 4898 (1961); 8, 373 (1943); and J. Amer.Chem.Soc. 73, 5068 (1951)).

The Michael addition of methyl acrylate onto nitro compounds of the general formula VII with the addition of a base, preferably benzyl-trimethylammonium hydroxide, is carried out in an alcohol, such as methanol, or tetrahydrofuran, but preferably in tert.-butanol or dioxan, at 0°-120° C., preferably at 10°-100° C.

Starting compounds of the formula XI in which $R^3$ and $R^4$ have the meanings given for formula I can be prepared from the bicyclic compounds of the formula X in which $R^3$ and $R^4$ have the meaning given for formula I:

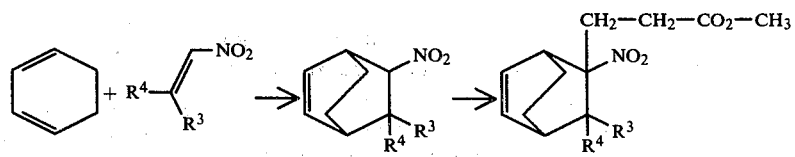

X

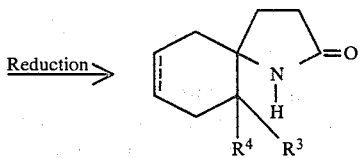

Reduction →

XI

The 2-nitrobicyclo[2.2.2]oct-5-enes X, which are known from the literature, can be prepared from the ω-nitrostyrenes and an excess of 1,3-cyclohexadiene. The starting compounds can be further processed in the crude form.

In addition to the compounds mentioned in the examples, compounds according to the invention which can be prepared are, preferably, the following: 5'-(4-phenylpiperidino)-3-phenyl-spiro[bicyclo[2.2.1]-heptane-2,2'-5-pyrroline], 3-phenyl-5'-thiamorpholino-spiro[bicyclo[2.2.1]-heptane-2,2'-5-pyrroline], 3-(4-chlorophenyl)-5'-(2-methylpiperidino)-spiro[bicyclo[2.2.1]-heptane-2,2'-5-pyrroline], 3-(4-chlorophenyl)-5'-(3-methylpiperidino)-spiro[bicyclo[2.2.1]-heptane-2,2'-5-pyrroline], 3-(4-chlorophenyl)-5'-(4-methylpiperidino)-spiro[bicyclo[2.2.1]-heptane-2,2'-5-pyrroline], 3-(4-chlorophenyl)-5'-(4-ethoxycarbonylpiperidino)-spiro[bicyclo[2.2.1]-heptane-2,2'-5-pyrroline], 3-(4-chlorophenyl)-5'-(2-methylmorpholine)-spiro[bicyclo[2.2.1]-heptane-2,2'-5-pyrroline], 3-(4-chlorophenyl)-5'-(3-methylmorpholino)-spiro[bicyclo[2.2.1]-heptane-2,2'-5-pyrroline], 3-(4-chlorophenyl)-5'-(2,6-dimethylmorpholino)-spiro[bicyclo[2.2.1]-heptane-2,2'-5-pyrroline], 3-(4-chlorophenyl)-5'-(2,5-dimethylmorpholino)-spiro[bicyclo[2.2.1]-heptane-2,2'-5-pyrroline], 3-(4-chlorophenyl)-5'-(2-methoxymorpholino)-spiro[bicyclo[2.2.1]-heptane-2,2'-5-pyrroline], 3-(4-chlorophenyl)-5'-(3-methoxymorpholino)-spiro[bicyclo[2.2.1]-heptane-2,2'-5-pyrroline], 3-(4-chlorophenyl)-5'-thiamorpholino-spiro[bicyclo[2.2.1]-heptane-2,2'-5-pyrroline], 3-(4-chlorophenyl)-5'-(3-carbethoxypiperidino)-spiro[bicyclo[2.2.1]-heptane-2,2'-5-pyrroline], 3-(4-chlorophenyl)-5'-(3-hydroxypiperidino)-spiro[bicyclo[2.2.1]-heptane-2,2'-5-pyrroline], 3-(4-chlorophenyl)-5'-(4-hydroxypiperidino)-spiro[bicyclo[2.2.1]-heptane-2,2'-5-pyrroline], 3-(4-chlorophenyl)-5'-(2-ethylpiperidino)-spiro[bicyclo[2.2.1]-heptane-2,2'-5-pyrroline], 3-(4-chlorophenyl)-5'-(2-methylpiperidino)-spiro[bicyclo[2.2.1]-heptane-2,2'-5-pyrroline], 3-(4-chlorophenyl)-5'-(3-methylpiperidino)-spiro[bicyclo[2.2.1]-heptane-2,2'-5-pyrroline], 3-(4-chlorophenyl)-5'-(4-methylpiperidino)-spiro[bicyclo[2.2.1]-heptane-2,2'-5-pyrroline], 3-(4-chlorophenyl)-5'-(2,2,6,6-tetramethylpiperidino)-spiro[bicyclo[2.2.1]-heptane-2,2'-5-pyrroline], 3-(4-chlorophenyl)-5'-(3-carbethoxypiperidino)-spiro[bicyclo[2.2.1]-heptane-2,2'-5-pyrroline], 3-(4-bromophenyl)-5'-pyrrolidino-spiro[bicyclo[2.2.1]-heptane-2,2'-5-pyrroline], 3-(4-bromophenyl)-5'-piperidino-spiro[bicyclo[2.2.1]-heptane-2,2'-5-pyrroline], 3-(4-bromophenyl)-5'-(4-phenylpiperidino)-spiro[bicyclo[2.2.1]-heptane-2,2'-5-pyrroline], 3-(4-bromophenyl)-5'-morpholino-spiro[bicyclo[2.2.1]-heptane-2,2'-5-pyrroline], 3-(4-bromophenyl)-5'-(2,6-dimethylmorpholino)-spiro[bicyclo[2.2.1]-heptane-2,2'-5-pyrroline], 3-(4-bromophenyl)-5'-(3-ethoxycarbonylmorpholino)-spiro[bicyclo[2.2.1]-heptane-2,2'-5-pyrroline], 5'-morpholino-3-(4-trifluoromethylphenyl)-spiro[bicyclo[2.2.1]-heptane-2,2'-5-pyrroline], 5'-(4-phenylpiperidino)-3-(4-trifluoromethylphenyl)-spiro[bicyclo[2.2.1]-heptane-2,2'-5-pyrroline], 5'-piperidino-3-(4-trifluoromethylphenyl)-spiro[bicyclo[2.2.1]-heptane-2,2'-5-pyrroline], 5'-pyrrolidino-3-(4-trifluoromethylphenyl)-spiro[bicyclo[2.2.1]-heptane-2,2'-5-pyrroline], 5'-piperazino-3-(4-trifluoromethylphenyl)-spiro[bicyclo[2.2.1]-heptane-2,2'-5-pyrroline], 5'-(2,6-dimethylmorpholino)-3-(4-trifluoromethylphenyl)-spiro[bicyclo[2.2.1]-heptane-2,2'-5-pyrroline], 5'-morpholino-3-(4-nitrophenyl)-spiro[bicyclo[2.2.1]-heptane-2,2'-5-pyrroline], 3-(4-nitrophenyl)-5'-piperidino-spiro[bicyclo[2.2.1]-heptane-2,2'-5-pyrroline], 3-(4-nitrophenyl)-5'-(4-phenylpiperidino)-spiro[bicyclo[2.2.1]-heptane-2,2'-5-pyrroline], 3-(4-nitrophenyl)-5'-(4-ethoxycarbonylpiperidino)-spiro[bicyclo[2.2.1]-heptane-2,2'-5-pyrroline], 3-(4-cyanophenyl)-5'-morpholino-spiro[bicyclo[2.2.1]-heptane-2,2'-5-pyrroline], 3-(4-cyanophenyl)-5'-piperidino-spiro[bicyclo[2.2.1]-heptane-2,2'-5-pyrroline], 3-(4-cyanophenyl)-5'-(4-phenylpiperidino)-spiro[bicyclo[2.2.1]-heptane-2,2'-5-pyrroline], 3-(4-methoxyphenyl)-5'-morpholino-spiro[bicyclo[2.2.1]-heptane-2,2'-5-pyrroline], 3-(4-methoxyphenyl)-5'-(2,6-dimethylmorpholino)-spiro[bicyclo[2.2.1]-heptane-2,2'-5-pyrroline], 3-(4-methoxyphenyl)-5'-piperidino-spiro[bicyclo[2.2.1]-heptane-2,2'-5-pyrroline], 3-(4-ethylphenyl)-5'-morpholino-spiro[bicyclo[2.2.1]-heptane-2,2'-5-pyrroline], 3-(4-ethylphenyl)-5'-piperidino-spiro[bicyclo[2.2.1]-heptane-2,2'-5-pyrroline], 3-(4-hydroxyphenyl)-5'-morpholino-spiro[bicyclo[2.2.1]-heptane-2,2'-5-pyrroline], 3-(4-hydroxyphenyl)-5'-piperidino-spiro[bicyclo[2.2.1]-heptane-2,2'-5-pyrroline], 3-(4-aminophenyl)-5'-morpholino-spiro[bicyclo[2.2.1]-heptane-2,2'-5-pyrroline], 3-(4-aminophenyl)-5'-piperiidino-spiro[bicyclo[2.2.1]-heptane-2,2'-5-pyrroline], 3-(4-methylaminophenyl)-5'-morpholino-spiro[bicyclo[2.2.1]-heptane-2,2'-5-pyrroline], 3-(4-methylaminophenyl)-5'-piperidino-spiro[bicyclo[2.2.1]-heptane-2,2'-5-pyrroline], 3-(2,3-dichlorophenyl)-5'-morpholino-spiro[bicyclo[2.2.1]-heptane-2,2'-5-pyrroline], 3-(2,4-dichlorophenyl)-5'-pyrrolidino-spiro[bicyclo[2.2.1]-heptane-2,2'-5-pyrroline], 3-(2,4-dichlorophenyl)-5'-piperidino-spiro[bicyclo[2.2.1]-heptane-2,2'-5-pyrroline], 3-(3,4-dichlorophenyl)-5'-morpholino-spiro[bicyclo[2.2.1]-heptane-2,2'-5-pyrroline], 3-(3,4-dichlorophenyl)-5'-piperidino-spiro[bicyclo[2.2.1]-heptane-2,2'-5-pyrroline], 3-(3,5-dichlorophenyl)-5'-morpholino-spiro[bicyclo[2.2.1]-heptane-2,2'-5-pyrroline], 3-methyl-5'-morpholino-3-phenyl-spiro[bicyclo[2.2.1]-heptane-2,2'-5-pyrroline], 3-(2-chlorophenyl)-3-methyl-5'-morpholino-spiro[bicyclo[2.2.1]-heptane-2,2'-5-pyrroline], 3-(4-chlorophenyl)-3-methyl-5'-morpholino-spiro[bicyclo[2.2.1]-heptane-2,2'-5-pyrroline], 3-(4-chlorophenyl)-3-methyl-5'-piperidino-spiro[bicyclo[2.2.1]-heptane-2,2'-5-pyrroline], 3-(4-chlorophenyl)-3-methyl-5'-(2,6-dimethylmorpholino)-spiro[bicyclo[2.2.1]-heptane-2,2'-5-pyrroline], 3-(4-bromophenyl)-3-methyl-5'-morpholino-spiro[bicyclo[2.2.1]-heptane- 2,2'-5-pyrroline], 3-(4-bromophenyl)-5'-(2,6-dimethylmorpholino)-3-methyl-spiro[bicyclo[2.2.1]-heptane-2,2'-5-pyrroline], 5'-(2,6-dimethylmorpholino)-3-methyl-3-(4-trifluoromethylphenyl)-spiro[bicyclo[2.2.1]-heptane-2,2'-5-pyrroline], 3-methyl-5'-morpholino-3-(4-trifluoro methylphenyl)-spiro[bicyclo[2.2.1]-heptane-2,2'-5-pyrroline], 3-methyl-5'-piperidino-3-(4-trifluoromethylphenyl)-spiro[bicyclo[2.2.1]-heptane-2,2'-5-pyrroline], 3-(4-cyanophenyl)-3-methyl-5'-morpholino-spiro[bicyclo[2.2.1]-heptane-2,2'-5-pyrroline], 3-(4-methoxyphenyl)-3-methyl-5'-morpholino-spiro[bicyclo[2.2.1]-heptane-2,2'-5-pyrroline], 3-(4-methylphenyl)-3-methyl-5'-morpholino-spiro[bicyclo[2.2.1]-heptane-2,2'-5-pyrroline], 3-(4-hydroxyphenyl)-3-methyl-5'-morpholino-spiro[bicyclo[2.2.1]-heptane-2,2'-5-pyrroline], 3-(4-aminophenyl)-3-methyl-5'-morpholino-spiro[bicyclo[2.2.1]-heptane-2,2'-5-pyrroline], 3-(2,3-dichlorophenyl)-3-methyl-5'-morpholino-spiro[bicyclo[2.2.1]-heptane-2,2'-5-pyrroline], 3-(2,4-dichlorophenyl)-3-methyl-5'-morpholino-spiro[bicyclo[2.2.1]-heptane-2,2'-5-pyrroline], 3-(3,4-dichlorophenyl)-3-methyl-5'-morpholino-spiro[bicyclo[2.2.1]-heptane-2,2'-5-pyrroline], 3-(4-fluorophenyl)-3-methyl-5'-morpholino-spiro[bicyclo[2.2.1]-heptane-2,2'-5-pyrroline], 3-ethyl-5'-morpholino-3-phenyl-spiro[bicyclo[2.2.1]-heptane-2,2'-5-pyrroline], 3-ethyl-5'-piperidino-3-phenyl-spiro[bicyclo[2.2.1]-heptane-2,2'-5-pyrroline], 3-(4-chlorophenyl)-3-ethyl-5'-morpholino-spiro[bicyclo[2.2.1]-heptane-2,2'-5-pyrroline], 3-(4-chlorophenyl)-3-ethyl-5'-piperidino-spiro[bicyclo[2.2.1]-heptane-2,2'-5-pyrroline], 5'-morpholino-3-phenyl-spiro[bicyclo[2.2.1]-hept-5-ene-2,2'-5-pyrroline], 3-phenyl-5'-piperidino-spiro[bicyclo[2.2.1]-hept-5-ene-2,2'-5-pyrroline], 3-phenyl-5'-piperazino-spiro[bicyclo[2.2.1]-hept-5-ene-2,2'-5-pyrroline], 3-phenyl-5-(4-phenylpiperidino)-spiro[bicyclo[2.2.1]-hept-5-ene-2,2'-5-pyrroline], 3-(4-chlorophenyl)-5'-morpholino-spiro[bicyclo[2.1.1]-hept-5-ene-2,2'-5-pyrroline], 3-(4-chlorophenyl)-5'-piperidino-spiro[bicyclo[2.2.1]-hept-5-ene-2,2'-5-pyrroline], 3-(4-chlorophenyl)-5'-piperazino-spiro[bicyclo[2.2.1]-hept-5-ene-2,2'-5-pyrroline], 3-(4-chlorophenyl)-5'-thiamorpholino-spiro[bicyclo[2.2.1]-hept-5-ene-2,2'-5-pyrroline], 3-(4-methylphenyl)-5'-morpholino-spiro[bicyclo[2.2.1]-hept-5-ene-2,2'-5-pyrroline], 3-(4-hydroxyphenyl)-5'-morpholino-spiro[bicyclo[2.2.1]-hept-5-ene-2,2'-5-pyrroline], 3-(4-aminophenyl)-5'-morpholino-spiro[bicyclo[2.2.1]-hept-5-ene-2,2'-5-pyrroline], 3-(2,4-dichlorophenyl)-5'-morpholino-spiro[bicyclo[2.2.1]-hept-5-ene-2,2'-5-pyrroline], 3-(3,4-dichlorophenyl)-5'-morpholino-spiro[bicyclo[2.2.1]-hept-5-ene-2,2'-5-pyrroline], 3-methyl-5'-morpholino-3-phenyl-spiro[bicyclo[2.2.1]-hept-5-ene-2,2'-5-pyrroline], 3-(4-chlorophenyl)-3-methyl-5'-morpholino-spiro[bicyclo[2.2.1]-hept-5-ene-2,2'-5-pyrroline], 3-(4-chlorophenyl)-3-methyl-5'-piperidino-spiro[bicyclo[2.2.1]-hept-5-ene-2,2'-5-pyrroline], 3-(4-chlorophenyl)-3-methyl-5'-pyrrolidino-spiro[bicyclo[2.2.1]-hept-5-ene-2,2'-5-pyrroline], 3-(4-chlorophenyl)-3-methyl-5'-thiamorpholino-spiro[bicyclo[2.2.1]-hept-5-ene-2,2'-5-pyrroline], 3-ethyl-5'-morpholino-3-phenyl-spiro[bicyclo[2.2.1]-hept-5-ene-2,2'-5-pyrroline], 3-(4-chlorophenyl)-3-ethyl-5'-morpholino-spiro[bicyclo[2.2.1]-hept-5-ene-2,2'-5-pyrroline], 3-(4-chlorophenyl)-5'-morpholino-spiro[bicyclo[2.2.2]-octane-2,2'-5-pyrroline], 3-(4-chlorophenyl)-5'-piperidino-spiro[bicyclo[2.2.2]-octane-2,2'-5-pyrroline], 3-(4-chlorophenyl)-5'-thiamorpholino-spiro[bicyclo[2.2.2]-octane-2,2'-5-pyrroline], 3-(4-bromophenyl)-5'-morpholino-spiro[bicyclo[2.2.2]-octane-2,2'-5-pyrroline], 3-(4-bromophenyl)-5'-piperidino-spiro[bicyclo[2.2.2]-octane-2,2'-5-pyrroline], 3-(4-bromophenyl)-5'-thiamorpholino-spiro[bicyclo[2.2.2]-octane-2,2'-5-pyrroline], 3-(4-fluorophenyl)-5'-morpholino-spiro[bicyclo[2.2.2]-octane-2,2'-5-pyrroline], 3-(4-fluorophenyl)-5'-piperidino-spiro[bicyclo[2.2.2]-octane-2,2'-5-pyrroline], 3-(4-fluorophenyl)-5'-thiamorpholino-spiro[bicyclo[2.2.2]-octane-2,2'-5-pyrroline], 5'-morpholino-3-(4-trifluoromethylphenyl)-spiro[bicyclo[2.2.2]-octane-2,2'-5-pyrroline], 5'-piperidino-3-(4-trifluoromethylphenyl)-spiro[bicyclo[2.2.2]-octane-2,2'-5-pyrroline], 5'-thiamorpholino-3-(4-trifluoromethylphenyl)-spiro[bicyclo[2.2.2]-octane-2,2'-5-pyrroline], 5'-morpholino-3-(4-nitrophenyl)-spiro[bicyclo[2.2.2]-octane-2,2'-5-pyrroline], 3-(4-nitrophenyl)-5'-piperidino-spiro[bicyclo[2.2.2]-octane-2,2'-5-pyrroline], 3-(4-hydroxyphenyl)-5'-morpholino-spiro[bicyclo[2.2.2]-octane-2,2'-5-pyrroline], 3-(4-hydroxyphenyl)-5'-piperidino-spiro[bicyclo[2.2.2]-octane-2,2'-5-pyrroline], 3-(4-cyanophenyl)-5'-morpholino-spiro[bicyclo[2.2.2]-octane-2,2'-5-pyrroline], 3-(4-cyanophenyl)-5'-piperidino-spiro[bicyclo[2.2.2]-octane-2,2'-5-pyrroline], 3-(4-dichlorophenyl)-5'-morpholino-spiro[bicyclo[2.2.2]-octane-2,2'-5-pyrroline], 3-(2,4-dichlorophenyl)-5'-piperidino-spiro[bicyclo[2.2.2]-octane-2,2'-5-pyrroline], 3-(3,4-dichlorophenyl)-5'-morpholino-spiro[bicyclo[2.2.2]-octane-2,2'-5-pyrroline], 3-(3,4-dichlorophenyl)-5'-piperidino-spiro[bicyclo[2.2.2]-octane-2,2'-5-pyrroline], 3-methyl-5'-morpholino-3-phenyl-spiro[bicyclo[2.2.2]-octane-2,2'-5-pyrroline], 3-methyl-3-phenyl-5'-piperidino-spiro[bicyclo[2.2.2]-octane-2,2'-5-pyrroline], 3-methyl-3-phenyl-5'-thiamorpholino-spiro[bicyclo[2.2.2]-octane-2,2'-5-pyrroline], 3-(4-chlorophenyl)-3-methyl-5'-morpholino-spiro[bicyclo[2.2.2]-octane-2,2'-5-pyrroline], 3-(4-chlorophenyl)-3-methyl-5'-piperidino-spiro[bicyclo[2.2.2]-octane-2,2'-5-pyrroline], 3-(4-chlorophenyl)-3-methyl-5'-thiamorpholino-spiro[bicyclo[2.2.2]-octane-2,2'-5-pyrroline], 5'-morpholino-3-phenyl-spiro[bicyclo[2.2.2]-oct-5-ene-2,2'-5-pyrroline], 3-(4-chlorophenyl)-5'-morpholino-spiro[bicyclo[2.2.2]-oct-5-ene-2,2'-5-pyrroline], 3-(4-bromophenyl)-5'-morpholino-spiro[bicyclo[2.2.2]-oct-5-ene-2,2'-5-pyrroline], 3-(4-fluorophenyl)-5'-morpholino-spiro[bicyclo[2.2.2]-oct-5-ene-2,2'-5-pyrroline], 5'-morpholino-3-(4-trifluoromethylphenyl)-spiro[bicyclo[2.2.2]-oct-5-ene-2,2'-5-pyrroline], 5'-morpholino-3-(4-nitrophenyl)-spiro[bicyclo[2.2.2]-oct-5-ene-2,2'-5-pyrroline], 3-(4-hydroxyphenyl)-5'-morpholino-spiro[bicyclo[2.2.2]-oct-5-ene-2,2'-5-pyrroline], 3-(4-cyanophenyl)-5'-morpholino-spiro[bicyclo[2.2.2]-oct-5-ene-2,2'-5-pyrroline], 3-(2,4-dichlorophenyl)-5'-morpholino-spiro[bicyclo[2.2.2]-oct-5-ene-2,2'-5-pyrroline] and 3-(3,4-dichlorophenyl)-5'-morpholino-spiro[bicyclo[2.2.2]-oct-5-ene-2,2'-5-pyrroline].

The compounds of the formula I can exist in four stereoisomeric forms and each stereoisomer can exist in two enantiomeric forms. It has now been found that in the preparation of the compounds of the formula I according to the invention, the stereoisomeric exo-aryl-endo-spiropyrroline compounds of the general formula XII

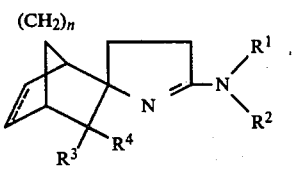

in which n, $R^1$, $R^2$, $R^3$ and $R^4$ have the meanings given for formula I, are formed as the main product. The configuration of the compounds of the general formula I is determined by the stereochemistry of the nitro-bicyclic compounds of the formulae XIII and XIV used as starting materials.

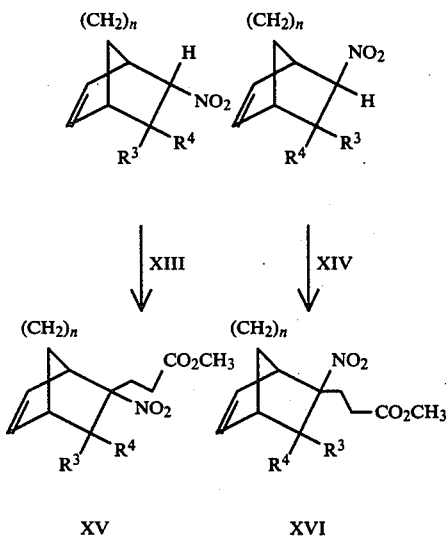

In the preparation of these nitro-bicyclic compounds, a mixture of the stereoisomers XIII and XIV is in general obtained, the exo-aryl-endo-nitro derivative of the formula XIII being present as the main product (determined by 1H-NMR spectroscopy). In the course of the further synthesis, in which the mixture of the nitro-bicyclic compounds is subjected to Michael addition of acrylate, the exo-aryl-endo-nitro ester of the formula XV is obtained as crystals, whilst the endo-aryl-exo-nitro compound of the formula XVI remains in the mother liquor.

It is also possible to use isomeric endo-aryl-exo-nitro-esters of the formula XVI, obtainable by purification by column chromatography of the mother liquors from exo-aryl-endo-nitro esters of the formula XV, as starting materials in the synthesis of the compounds according to the invention, which, by an analogous synthesis route, leads to compounds according to the invention, the stereochemistry of which can be represented by the formula XVII as endo-aryl-exo-pyrroline products

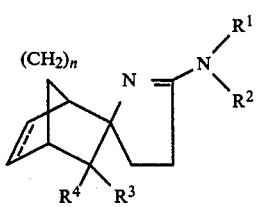

in which n, $R^1$, $R^2$, $R^3$ and $R^4$ have the meanings given for formula I.

It has furthermore been found that the optical isomers of the heterocyclic spiro-linked amidines of the formulae XII and XVII display surprisingly unusual differences in their biological activity. Thus, for example, the anti-depressant activity of the laevorotatory isomer is more highly pronounced, whilst the dextro-rotatory isomer has a weaker action than the racemate. The present invention thus also relates to optically active stereoisomers of compounds of the general formulae XII and XVII in which $R^1$, $R^2$, $R^3$ and $R^4$ have the meanings indicated for formula I, as well as the acid addition salts thereof, processes for the preparation of these compounds and pharmaceutical formulation containing them.

Particularly preferred optically active stereoisomers are: (−)-3-exo-(4-chlorophenyl)-5′-morpholino-spiro[bicyclo[2.2.1]-heptane-2,2′-5-endo-pyrroline], (−)-3-endo-(4-chlorophenyl)-5′-morpholino-spiro[bicyclo[2.2.1]-heptane-2,2′-5-exo-pyrroline], (−)-3-exo-(4-chlorophenyl)-5′-morpholino-spiro[bicyclo[2.2.1]-hept-5-ene-2,2′-5-endo-pyrroline], (−)-3-endo-(4-chlorophenyl)-5′-morpholino-spiro[bicyclo[2.2.1]-hept-5-ene-2,2′-5-exo-pyrroline], (−)-3-exo-(4-fluorophenyl)-5′-morpholino-spiro[bicyclo[2.2.1]-heptane-2,2′-5-endo-pyrroline], (−)-3-endo-(4-fluorophenyl)-5′-morpholino-spiro[bicyclo[2.2.1]-heptane-2,2′-5-exo-pyrroline], (−)-3-exo-(4-fluorophenyl)-5′-morpholino-spiro[bicyclo[2.2.1]-hept-5-ene-2,2′-5-endo-pyrroline], (−)-3-endo-(4-fluorophenyl)-5′-morphilino-spiro[bicyclo[2.2.1]-hept-5-ene-2,2′-5-exo-pyrroline], 3-exo-(4-bromophenyl)-5′-morpholino-spiro[bicyclo[2.2.1]-heptane-2,2′-5-endo-pyrroline], 3-endo-(4-bromophenyl)-5′-morpholino-spiro[bicyclo[2.2.1]-heptane-2,2′-5-exo-pyrroline], 5′-morpholino-3-exo-(4-trifluoromethylphenyl)-spiro[bicyclo[2.2.1]-heptane-2,2′-5-endo-pyrroline] and 5′-morpholino-3-endo(4-trifluoromethylphenyl)-sprio[bicyclo[2.2.1]-heptane-2,2′-5-exo-pyrroline].

The optical isomers according to the invention can be prepared by resolving either a racemic compound of the abovementioned formulae XII and XVII, in which n, $R^1$, $R^2$, $R^3$ and $R^4$ have the meanings indicated, or a racemic precurser thereof into the optical isomers by a standard process, and if necessary converting the optically active precurser thus obtained into the desired compounds of the formulae XII or XVII. Preferably, a racemic mixture of a compound of the abovementioned formulae XII and XVII is resolved into the optical isomers by a standard resolution process, such as is described in the literature.

The resolution can, of course, also be carried out with a racemic mixture of the end product or with a racemate of an intermediate compound of the general formula V, in which case one or both of the optical isomers ar reacted further.

However, the resolution is in general carried out on a racemic mixture of the basic compound of the general formula XII and XVII by processes described in the literature, for example using an optically active acid. Thus, for example, a solution of the racemate in a suitable solvent, for example an alcohol, is treated with a solution of an optically active acid in order to effect crystallization of the salt of a specific enantiomer. If required, the other enantiomer can frequently be prepared from the mother liquors, if desired by treatment with a base and then with the other optical isomer of the optically active acid, or it is also possible to treat a fresh solution of the racemate with a solution of the other enantiomorph of the optically active acid. The particular solvent to be used in an individual case and the particular optically active acid to be used cannot be generally predicted and the correct choice is made with the aid of simple experiments. The best combination is that whereby it is possible to isolate the salt in a highly pure state (that is to say free from the other enantiomer) and as crystals.

It has now been found that D(−)- and L(+)-tartaric acid, D(−)- and L(+)-dibenzoyltartaric acid and D(−)- and L(+)-di-p-tolyltartaric acid are very particularly suitable for the resolution of some compounds of the formulae XII and XVII.

Thus, if the pure salt of an isomer has been isolated, this is then treated with a strong base, for examle ammonium hydroxide or a solution of sodium hydroxide or sodium carbonate, in order to liberate the free base of the optically active amidine.

The compounds of the formula I or their stereoisomers of the formulae XII and XVII can be isolated as such or in the form of an acid addition salt by the processes described. The salts are preferably the pharmaceutically acceptable, non-toxic addition salts with suitable acids, such as, for example, those with inorganic acids, such as hydrochloric acid, hydrobromic acid and hydriodic acid, nitric acid, sulfuric acid or phosphoric acid, or with organic acids, such as formic acid, acetic acid, propionic acid, succinic acid, tartaric acid, glycolic acid, lactic acid, malonic acid, hydroxymaleic acid, fumaric acid, oxalic acid, citric acid, malic acid, mucic acid, benzoic acid, salicylic acid, aceturic acid, embonic acid, naphthalene-1,5-disulfonic acid, ascorbic acid, phenylacetic acid, p-amino-salicyclic acid, hydroxyethanesulfonic acid or benzenesulfonic acid, or synthetic resins which contain acid groups, for example those which have an ion exchanger effect.

The acid addition salt thereby obtained can be converted into the free compound by known processes, for example by treatment with a base, such as a metal hydroxide, metal alcoholate or metal carbonate, with ammonia or with a hydroxyl ion exchanger, or with any other suitable reagent. A resulting acid addition salt can be converted into another salt by known processes; thus, for example, a salt with an inorganic acid can be treated with a metal salt, such as, for example, a sodium salt, barium salt or silver salt, of and acid in a suitable diluent in which the resulting inorganic salt is insoluble and the inorganic salt is thereby removed from the reaction medium. An acid addition salt can also be converted into another acid addition salt by treatment with an anion exchanger preparation. A quaternary ammonium salt can be prepared by reacting the free base with an alkyl halide.

U.S. Pat. No. 2,931,805 describes other spironorbornanes which have a hypotensive, vasodilatory and local anaesthetic action and an action on the central nervous system. However, it was not to be expected that the spiro compounds according to the invention would have a powerful anti-depressant action.

When administered intraperitoneally or orally, the compounds according to the invention and their pharmacologically acceptable salts antagonize tetrabenazine ptosis in mice, with an $ED_{50}$ of 0.1–10 mg/kg: the appropriate amount of a 1% strength homogenate of the test substance (in carboxymethylcellulose) in a 0.9% strength NaCl solution (in distilled water) is administered to five male animals weighing 22 g, whereupon the ptosis caused by tetrabenazine administered beforehand is cured.

The anti-depressant activity and their use for the treatment of various depressive states in mammals was furthermore demonstrated with the aid of the inhibition of the resorption of noradrenalin and dopamine in cases of cerebral synaptosomes in mice.

The compounds have a low toxicity. The $LD_{50}$ values are in general between 100–500 mg/kg on oral administration (mice).

The compounds according to the invention and their pharmaceutically acceptable salts are active within a broad dosage range, the particular dose administered depending on various factors, such as, for example, the particular compound used and the condition, type and size of the mammal to be treated. The dose required per day is usually within the range from 10 to 60 mg in the treatment of adult humans.

Individual doses of 0.1–5 mg per kg are appropriate in the treatment of test animals, such as mice and rats. The active compounds according to the invention and their salts are usually administered orally or by injection, and for this purpose these compounds and salts are as a rule used in the form of a pharmaceutical preparation. These pharmaceutical agents are prepared in a manner which is in itself known in this field, and they usually contain at least one compound according to the invention or a salt thereof in combination with a pharmaceutically acceptable excipient suitable for this purpose. To prepare the pharmaceutical agents according to the invention, the active constituent is as a rule mixed with an excipient or diluted with an excipient or enclosed in an excipient, which can be in the form of a capsule, in the form of a sachet or in the form of another container; if the excipient serves as the diluent, it can be a solid, semi-solid or liquid material which is used as a diluent, auxiliary or medium for the active constituent (active compound). Examples of suitable excipients are lactose, dextrose, sucrose, sorbitol, mannitol, starch, gum acacia, calcium phosphate, alginates, tragacanth, gelatin, syrup, methylcellulose, methyl and propyl hydroxybenzoate, talc, magnesium stearate or mineral oil.

The pharmaceutical agents according to the invention can be formulated in a manner which is in itself known such that they release the active compound, after administration, to the patient rapidly, continuously or in a delayed manner.

Depending on the nature of the administration, the pharmaceutical agents indicated above can be processed to tablets, capsules or suspensions for oral use and to injection solutions for parenteral use.

The invention accordingly furthermore relates to a pharmaceutial agent (preparation), which contains at least one compound of the formula I or a pharmaceutically acceptable acid addition salt thereof in combination with a pharmaceutically acceptable excipient suitable for this purpose.

According to another aspect, the present invention relates to a process for the treatment of depressive states in mammals, in particular humans, which comprises administering a compound of the formula I, or of a pharmaceutically acceptable salt thereof, to the sick person in an amount having an anti-depressant effect.

EXAMPLE 1

3-(2-Methoxyphenyl)-5'-pyrrolidino-spiro[bicyclo[2.2.1]-heptane-2,2'-5-pyrroline]hydriodide (a) Methyl β-[3-(2-methoxyphenyl)-2-nitro-bicyclo[2.2.1]-hept-5-en-2-yl]-propionate (1) 0.1 mol of 3-(2-methoxyphenyl)-2-nitro-bicyclo[2.2.1]-hept-5-ene are dissolved in 600 ml of dioxan with the addition of 12 ml of Triton B and 0.1 mol of methyl acrylate and the solution is heated to the boiling point until the reaction is complete (monitoring by thin layer chromatography). After stripping off the solvents, the residue is recrystallized from ethanol, with the addition of animal charcoal. Colorless crystals of melting point 72°-76° C.

(2) 0.4 mole of methyl acrylate is added to a mixture of 0.4 mole of 3-(2-methoxyphenyl)-2-nitro-bicyclo[2.2.1]-hept-5-ene, 40 ml of tert.-butanol and 6 ml of Triton B solution (40% strength in methanol) at +5° C., whilst stirring. The mixture is subsequently stirred at room temperature for 3 hours, the temperature increasing to 40° C. for a short time. After diluting the mixture with ethanol and neutralizing it with a little dilute hydrochloric acid, the precipitate is filtered off. After recrystallization from ethanol, colorless crystals of melting point 72°-76° C. are obtained.

(b) 3-(2-Methoxyphenyl)-spiro[bicyclo[2.2.1]-heptane-2,2'-pyrrolidin]-5'-one 0.2 mole of methyl β-[3-(2-methoxyphenyl)-2-nitrobicyclo[2.2.1]-hept-5-en-2-yl]-propionate is dissolved in 800 ml of ethanol and, after adding 2 spatulas of Raney nickel, is hydrogenated at 50° C. and under 70 bars for 24 hours. The catalyst is filtered off, the solvent is evaporated off in a rotary evaporator and the residue is recrystallized from isopropanol. Colorless crystals of melting point 260° C.

(c) 3-(2-Methoxyphenyl)-spiro[bicyclo[2.2.1]-heptane-2,2'-pyrrolidine]-5'-thione 90 mmoles of 3-(2-methoxyphenyl)-spiro[bicyclo[2.2.1]-heptane-2,2'-pyrrolidin]-5'-one, 10 g of phosphorous pentasulfide and 9 g of calcium oxide are suspended in 260 ml of toluene and the suspension is stirred at a bath temperature of 50° C. for 2 hours. It is filtered hot into a saturated sodium carbonate solution and the residues are extracted three times by boiling with toluene. The insoluble residues are dissolved in concentrated hydrochloric acid and the solution is diluted with water and transferred to a separating funnel, together with the alkaline filtrate and the toluene extracts. After shaking the mixture vigorously, the organic layer is separated off and the hydrochloric acid phase is extracted again with toluene. The combined organic phases are dried over sodium sulfate and concentrated in vacuo. Recrystallization from ethyl acetate gives colorless crystals of melting point 194° C.

(d) 3-(2-Methoxyphenyl)-5'-methylthio-spiro[bicyclo[2.2.1]-heptane-2,2'-5-pyrroline]hydriodide 56 mmoles of 3-(2-methoxyphenyl)-spiro[bicyclo[2.2.1]-heptane-2,2'-pyrrolidine]-5'-thione and 7 ml of methyl iodide in 220 ml of acetone are refluxed for 10 minutes. After cooling the mixture, the residue is filtered off. Pale yellow compound of melting point 228° C. (decomposition)

(e) 3-(2-Methoxyphenyl)-5'-pyrrolidino-spiro[bicyclo[2.2.1]-heptane-2,2'-5-pyrroline]hydriodide 12 mmoles of 3-(2-methoxyphenyl)-5'-methylthio-spiro[bicyclo[2.2.1]-heptane-2,2'-5-pyrroline]hydriodide and 2 g of pyrrolidine in 50 ml of ethanol are refluxed. The solvent is stripped off and the residue obtained is recrystallized from isopropanol. Colorless crystals of melting point 228° C.

The compound thus prepared is an exo-aryl-endo-spiropyrroline compound from a stereochemical point of view, as also are all the other compounds of Table 1, which were prepared analogously.

Unless otherwise indicated, in the following text, the heterocyclic spiro-linked amidines and their precursors have the exo-aryl-endo-pyrroline configuration.

TABLE 1

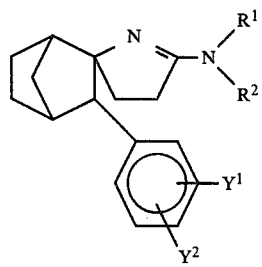

| Example | $Y^1$ | $Y^2$ | $-N\begin{subarray}{l}R^1\\R^2\end{subarray}$ | Salt | Melting point/decomposition |
|---|---|---|---|---|---|
| 2 | H | H | —NH—n-butyl | HI | 165–167° C. |
| 3 | H | H | —NH—(CH$_2$)$_2$—N(C$_2$H$_5$)(C$_2$H$_5$) | hydrogen naphthalene-1,5-disulfonate | 266–267° C. |
| 4 | H | H | —NH—benzyl | HI | 203–205° C. |

TABLE 1-continued

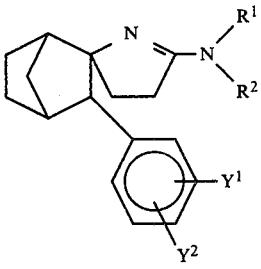

| Example | Y¹ | Y² | $-N\begin{smallmatrix}R^1\\R^2\end{smallmatrix}$ | Salt | Melting point/ decomposition |
|---|---|---|---|---|---|
| 5 | H | H | —NH—(CH₂)₂—C₆H₅ | HI | 153–155° C. |
| 6 | H | H | —NH—(CH₂)₂—(2-OCH₃-C₆H₄) | hydrogen naphthalene-1,5-disulfonate | 144–150° C. |
| 7 | H | H | —NH—(CH₂)₂—(3,4-di-OCH₃-C₆H₃) | — | 114° C. |
| 8 | H | H | —NH—CH₂—C(C₂H₅)₂—(3-OCH₃-C₆H₄) | hydrogen fumarate | 177° C. |
| 9 | H | H | —NH—(CH₂)₂—C(CH₃)—C₂H₅ | HI | 190° C. |
| 10 | H | H | —N(CH₂—CH₂—OH)₂ | hydrogen oxalate | 130° C. |
| 11 | H | H | —N(CH₃)(CH₂—CHOH—CH₃) | hydrogen naphthalene-1,5-disulfonate | 240–242° C. |
| 12 | H | H | —NH—C₆H₁₁ | HI | 227–228° C. |
| 13 | H | H | —NH—cyclooctyl | hydrogen oxalate | 217° C. |
| 14 | H | H | —NH—(CH₂)₃—N(piperazinyl)—(3-CH₃-C₆H₄) | — | 127° C. |
| 15 | H | H | pyrrolidin-1-yl | hydrogen oxalate | 96° C. |
| 16 | H | H | piperidin-1-yl | DL-hydrogen tartrate | 238° C. |
| 17 | H | H | morpholin-4-yl | hydrogen maleate | 173° C. |
| 18 | H | H | 4-methylpiperazin-1-yl | hydrogen maleate hydriodide | 201° C. |
| 19 | H | H | 4-ethoxycarbonylpiperazin-1-yl | hydrogen maleate | 190° C. |

TABLE 1-continued

[Structure: bicyclic (norbornane) system fused to a dihydropyrrole ring with =N–NR¹R² substituent; the bridgehead carbon bears a phenyl group with substituents Y¹ and Y²]

| Example | Y¹ | Y² | –NR¹R² | Salt | Melting point/decomposition |
|---|---|---|---|---|---|
| 20 | H | H | –N(piperazin-1-yl)–N'–(CH₂)₂OH | di(hydrogen maleate) | 198–200° C. |
| 21 | H | H | –N(piperazin-1-yl)–N'–(2-methylphenyl) | HI | 245° C. |
| 22 | H | H | –N(piperazin-1-yl)–N'–benzyl | di(hydrogen maleate) | 215° C. |
| 23 | H | H | –N(piperazin-1-yl)–N'–C(=O)–phenyl | HI | 160° C. |
| 24 | H | 2 Cl– | –N(pyrrolidin-1-yl) | hydrogen fumarate | 230° C. |
| 25 | H | 2 Cl– | –N(piperidin-1-yl) | hydrogen naphthalene-1,5-disulfonate | 278° C. |
| 26 | H | 2 Cl | –N(morpholin-4-yl) | DL-hydrogen tartrate | 225° C. |
| 27 | H | 2-OCH₃ | –N(piperidin-1-yl) | hydrogen naphthalene-1,5-disulfonate | 255° C. |
| 28 | H | 2-OCH₃ | –N(morpholin-4-yl) | hydrogen naphthalene-1,5-disulfonate | 127° C. |
| 29 | 3-OCH₃ | 4-OCH₃ | –N(morpholin-4-yl) | hydrogen napthalene-1,5-disulfonate | 114–116° C. |
| 30 | H | 4-Cl | –N(pyrrolidin-1-yl) | D,L-hydrogen tartrate | 236° C. |
| 31 | H | 4-Cl | –N(piperidin-1-yl) | D,L-hydrogen tartrate | 218–220° C. |
| 32 | H | 4-Cl | –N(morpholin-4-yl) | D,L-hydrogen tartrate | 237° C. (decomposition) |
| 33 | H | 4-Cl | –N(piperazin-1-yl)–N'–H | D,L-hydrogen tartrate | 205° C. |

TABLE 1-continued

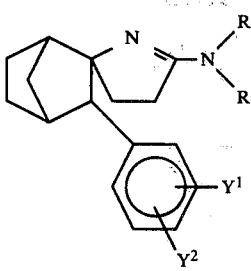

| Example | Y¹ | Y² | -N(R¹)(R²) | Salt | Melting point/ decomposition |
|---|---|---|---|---|---|
| 34 | H | 4-Cl | -N(piperazinyl)N—CH₃ | D,L-hydrogen tartrate | 211° C. |
| 35 | H | 4-Cl | -N(piperazinyl)N—(CH₂)₂OH | D,L-hydrogen tartrate | 216–218° C. |
| 36 | H | 4-Cl | -N(piperazinyl)N—(3-Cl-phenyl) | D,L-hydrogen tartrate | 225–232° C. |
| 37 | H | 2-OCH₃ | -N(CH₃)(CH₂—CHOH—CH₃) | hydrogen naphthalene-1,5-disulfonate | 273–276° C. |
| 38 | H | 4-Cl | -N(CH₃)(CH₂—CHOH—CH₃) | DL-hydrogen tartrate | 176–179° C. |
| 39 | H | 4-Cl | -N(piperazinyl)N—H | DL-dihydrogen tartrate | 223° C. |
| 40 | H | 4-CH₃ | -N(piperidinyl) | DL-hydrogen tartrate | 189–191° C. |
| 41 | H | 4-CH₃ | -N(morpholinyl) | DL-hydrogen tartrate | 235–236° C. |
| 42 | H | 4-CH₃ | -N(piperazinyl)N—CH₃ | DL-hydrogen tartrate | 195–197° C. |
| 43 | H | 4-Cl | -N(4-phenylpiperidinyl) | HI | 223–224° C. |
| 44 | H | 4-F | -N(piperidinyl) | DL-hydrogen tartrate | 220–221° C. |
| 45 | H | 4-F | -N(morpholinyl) | DL-hydrogen tartrate | 234° C. |
| 46 | H | 4-F | -N(piperazinyl)N—CH₃ | DL-hydrogen tartrate | 212–214° C. |
| 47 | 3-Cl | 4-Cl | -N(piperidinyl) | HI | 224–226° |

TABLE 1-continued

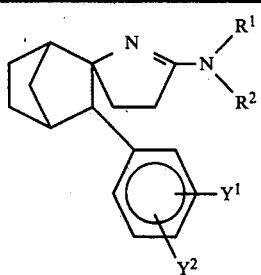

| Example | Y¹ | Y² | —NR¹R² | Salt | Melting point/decomposition |
|---|---|---|---|---|---|
| 48 | 3-Cl | 4-Cl | —N(morpholino) | HI | 224–225° |
| 49 | 2-Cl | 4-Cl | —N(piperidino) | DL-hydrogen tartrate | 199–201° C. |
| 50 | 2-Cl | 4-Cl | —N(morpholino) | DL-hydrogen tartrate | 202–205° C. |
| 51 | H | 4-NH₂ | —N(piperidino) | — | 151–155° C. |
| 52 | 4-Br | H | —N(morpholino) | D,L-hydrogen tartrate | 225–227° C. |
| 53 | 4-F | H | —N(piperazino-NH) | D,L-hydrogen tartrate | 212° C. decomposition |
| 54 | 4-F | H | —N(4-phenylpiperidino) | hydriodide | 220–224° C. |
| 55 | 3-Cl | H | —N(morpholino) | — | 170° C. |
| 56 | 4-Cl | H | —N(4-OH-4-C₆H₅-piperidino) | hydriodide | 236–238° C. |
| 57 | 4-Cl | H | —N(thiomorpholino) | D,L-hydrogen tartrate | 233° C. decomposition |
| 58 | 4-Cl | H | —N(thiomorpholino-SO) | D,L-hydrogen tartrate | 261–263° C. |
| 59 | 4-Cl | H | —N(4-(benzimidazolin-2-on-1-yl)piperidino) | hydriodide | 316° C. decomposition |
| 60 | 4-Cl | H | —N(4-benzamido-piperidino) | — | 198–200° C. |
| 61 | 4-Cl | H | -homopiperidino | D,L-hydrogen tartrate | 248° C. decomposition |

TABLE 1-continued

| Example | Y¹ | Y² | −N(R¹)(R²) | Salt | Melting point/ decomposition |
|---|---|---|---|---|---|
| 62 | 4-Cl | H | −NH−NH−CH₂−(phenyl-OH) | — | 219–222° C. |
| 63 | 4-Cl | H | spiro piperidine-piperazine with C(=O)NH and N−C₆H₅ | — | 238–240° C. |
| 64 | 4-Cl | H | −N(piperazine)N−(CH₂)₃−C(=O)−(4-F-phenyl) | — | 300° C. decomposition |
| 65 | 4-Cl | H | 3,5-dimethylmorpholino | hydriodide | 288° C. decomposition |
| 66 | 4-Cl | H | −NH−(CH₂)₂−morpholino | oxalate | 219° C. |
| 67 | 4-OCH₃ | H | morpholino | HI | 268–270° C. |
| 68 | 4-OCH₃ | H | piperidino | hydrogen tartrate(D,L) | 203–204° C. |
| 69 | 4-OC₂H₅ | H | morpholino | hydrogen tartrate(D,L) | 248° C. decomposition |
| 70 | 4-OC₂H₅ | H | piperidino | hydrogen tartrate (D,L) | 206° C. decomposition |
| 71 | 4-CF₃ | H | morpholino | HI | 254–255° C. |
| 72 | 4-CF₃ | H | piperidino | hydrogen tartrate (D,L) | 220° C. decomposition |

The compound of Example 73 is also prepared analogously to Example 1:

EXAMPLE 73

5′-Morpholino-3-exo-thienyl-spiro[bicyclo[2.2.1]-heptane-2,2′-5-endo-pyrroline] hydriodide, pale yellow crystals of melting point 137°–140° C.

EXAMPLE 74

5'-Amino-3-phenyl-spiro[bicyclo[2.2.1]-heptane-2,2'-5-pyrroline] hydrogen fumarate 50 mmoles of 5'-methylthio-3-phenyl-spiro[bicyclo[2.2.1]-heptane-2,2'-5-pyrroline] hydriodide are treated with 250 ml of aqueous ammonia at 70° C. and under a nitrogen pressure of 80 bars for 24 hours. After stripping off the solvent, an oil which slowly solidifies is obtained. After conversion into the addition salt of fumaric acid, colorless crystals of melting point 242° C. (from methanol/water 1:1) are obtained.

EXAMPLE 75

5'-Morpholino-3-phenyl-spiro[bicyclo[2.2.1]-hept-5-ene-2,2'-5-pyrroline] hemi-naphthalene-1,5-disulfonate (a) 3-Phenyl-spiro[bicyclo[2.2.1]-hept-5-ene-2,2'-pyrrolidin]-5'-one 0.17 mole of methyl 2-nitro-3-phenyl-bicyclo[2.2.1]-hept-5-en-2-yl]-propionate (literature: U.S. Pat. No. 2,931,805) and 100 g of tin powder in 1.3 l of glacial acetic acid are stirred at 100°–110° C. for 3 hours. After cooling the mixture, it is neutralized with sodium carbonate solution and extracted twice with ether. The organic phase is separated off, dried over sodium sulfate and evaporated in vacuo. Recrystallization of the residue from a little methanol gives colorless crystals of melting point 152°–155° C.

(b) 3-Phenyl-spiro[bicyclo[2.2.1]-hept-5-ene-2,2'-pyrrolidine]-5'-thione 20 mmoles of 3-phenyl-spiro[bicyclo[2.2.1]-hept-5-ene-2,2'-pyrrolidin]-5'-one, 4 g of phosphorus pentasulfide and 3 g of calcium oxide are stirred at 50° C. for 2 hours and the mixture is filtered hot into a saturated sodium carbonate solution. The residue is substantially disintegrated with concentrated hydrochloric acid, the mixture is diluted with water and the solutions are combined. The mixture is extracted several times by shaking with toluene and the organic phases are separated off, dried and evaporated in vacuo. Recrystallization of the residue from ethyl acetate gives colorless crystals of melting point 204° C. (decomposition).

(c) 5'-Methylthio-3-phenyl-spiro[bicyclo[2.2.1]-hept-5-ene 2,2'-5-pyrroline] hydriodide 6 mmoles of 3-phenyl-spiro[bicyclo[2.2.1]-hept-5-ene-2,2'-pyrrolidine]-5'-thione are dissolved in 30 ml of acetone, 1 ml of methyl iodide is added and the mixture is refluxed for 10 minutes. After cooling, the precipitate is filtered off. The crystalline compound, which is pure according to a thin layer chromatogram, is further processed immediately.

(d) 5'-Morpholino-3-phenyl-spiro[bicyclo[2.2.1]-hept-5-ene-2,2'-5-pyrroline] hemi-naphthalene-1,5-disulfonate 5 mmoles of 5'-methylthio-3-phenyl-spiro[bicyclo[2.2.1]-hept-5-ene-2,2'-5-pyrroline] hydriodide and 2 ml of morpholine in 30 ml of ethanol are refluxed for 1 hour and the solvent is stripped off. After extracting the mixture by shaking with saturated sodium carbonate solution/ether, the organic phase is separated off, dried and concentrated on a rotary evaporator. The residue gives, after conversion into the addition salt of 1,5-naphthalenedisulfonic acid, colorless crystals of decomposition point 261° C. (from methanol).

EXAMPLE 76

3-Phenyl-5'-piperidino-spiro[bicyclo[2.2.1]-hept-5-ene-2,2'-5-pyrroline] hemi-naphthalene-1,5-disulfonate can be prepared analogously to Example 75 in the form of colorless crystals of melting point 176° C.

The compounds of the following Examples 77 and 78 were prepared analogously to Example 75.

EXAMPLE 77

3-exo-(4-Chlorophenyl)-5'-morpholino-spiro[bicyclo[2.2.1]-hept-5-ene-2,2'-5-endo-pyrroline] hydriodide, colorless crystals of melting point 253° C. (decomposition).

EXAMPLE 78

3-exo-(4-Chlorophenyl)-5'-piperidino-spiro[bicyclo[2.2.1]-hept-5-ene-2,2'-5-endo-pyrroline] hydriodide, colorless crystals of melting point 190° C.

EXAMPLE 79

5'-Morpholino-3-phenyl-spiro[bicyclo[2.2.2]-octane-2,2'-5-pyrroline] hemi-naphthalene-1,5-disulfonate (a) 2-Nitro-3-phenyl-bicyclo[2.2.2]-oct-5-ene 45.1 g of 1,3-cyclohexadiene (EMKA), 41.9 g of ω-nitrostyrene, 60 g of o-xylene and 1 pinch of hydroquinone are treated in an autoclave at 200° C. and under a nitrogen pressure of 60 bar for 24 hours. The solvent is stripped off and the residue is distilled under a high vacuum. Boiling point $_{0.05}$=120°–160° C.

(b) Methyl β-(2-nitro-3-phenyl-bicyclo[2.2.2]-oct-5-en-2-yl)-propionate

Variant A: 0.14 mole of 2-nitro-3-phenyl-bicyclo[2.2.2]-oct-5-ene is dissolved in 50 ml of dioxan, with the addition of 27 ml of Triton B and 0.14 mole of methyl acrylate, and the mixture is refluxed until the reaction is complete (4 hours). After stripping off the solvent, the residue crystallizes completely. Recrystallization from isopropanol gives crystals of melting point 127°–132° C.

Variant B: 0.18 mole of 2-nitro-3-phenyl-bicyclo[2.2.2]-oct-5-ene, 0.18 mole of methyl acrylate and 3.8 ml of Triton B in 50 ml of tert.-butanol and stirred for 24 hours, a further 0.18 mole of methyl acrylate and 70 ml of dioxan are then added and the mixture is heated to the reflux temperature for 24 hours. After cooling, the reaction mixture crystallizes. A little ethanol is added, the mixture is neutralized with 2 N hydrochloric acid and the crystal sludge is filtered. Recrystallization of the crystals from isopropanol with the addition of animal charcoal gives crystals of melting point 127°–131° C.

(c) 3-Phenyl-spiro[bicyclo[2.2.2]-octane-2,2'-pyrrolidin]-5'-one 55 mmoles of methyl β-(2-nitro-3-phenyl-bicyclo[2.2.2]-oct-5-en-2-yl)-propionate in 100 ml of ethanol are hydrogenated, with 3 g of Raney nickel, at 50° C. and under 70 bars. The catalyst is filtered off, the solvent is evaporated off and the residue is recrystallized from isopropanol.

(d) 3-Phenyl-spiro[bicyclo[2.2.2]-octane-2,2'-pyrrolidin]-5'-thione 33 mmoles of 3-phenyl-spiro[bicyclo[2.2.2]-octane-2,2'-pyrrolidin]-5'-one are dispersed in 200 ml of toluene, and a mixture of 7.3 g of phosphorus pentasulfide and 7 g of calcium oxide is added, whilst stirring, and the mixture is stirred at 50° C. for 2½ hours. The hot reaction solution is filtered into a saturated sodium carbonate solution. The residues are dissolved in concentrated hydrochloric acid and the solution is diluted with water and carefully combined with the toluene/sodium carbonate mixture. The aqueous phase is extracted several times with toluene and the extracts are combined, dried and concentrated in vacuo. Recrystallization of the residue from a little ethyl acetate gives colorless crystals.

(e) 5'-Methylthio-3-phenyl-spiro[bicyclo[2.2.2]-octane-2,2'-5-pyrroline] hydriodide 24 mmoles of 3-phenyl-spiro[bicyclo[2.2.2]-octane-2,2'-pyrrolidine]-5'-thione and 3 ml of methyl iodide are heated in 50 ml of acetone for 10 minutes. After cooling, the mixture is filtered. Crystals of melting point 192°–193° C. are obtained.

(f) 5'-Morpholino-3-phenyl-spiro[bicyclo[2.2.2]-octane-2,2'-5-pyrrolina] hemi-naphthalene-1,5-disulfonate 10 mmoles of 5'-methylthio-3-phenyl-spiro[bicyclo[2.2.2]-octane-2,2'-5-pyrroline] hydriodide and 2 g of morpholine in 80 ml of ethanol are refluxed for 9 hours, the solvent is stripped off and the residue is treated with a mixture of 4 N potassium hydroxide solution and ethyl acetate. The organic phase is separated off, dried and concentrated on a rotary evaporator. The addition salt of napthalene-1,5-disulfonic acid melts at 299°–300° C.

The compounds of Examples 80 and 81 are prepared analogously to Example 79.

EXAMPLE 80

3-exo-(4-Chlorophenyl)-5'-morpholino-spiro[bicyclo[2.2.2]-octane-2,2'-5-endo-pyrroline], pale yellow oil with $R_f = 0.23$, thin layer chromatography on silica gel, $CHCl_3/EtOH = 9:1$.

EXAMPLE 81

5'-Piperidino-3-phenyl-spiro[bicyclo[2.2.2]-octane-2,2'-5-pyrroline] hemi-naphthalene-1,5-disulfonate hemihydrate of melting point 298°–299° C.

EXAMPLE 82

3-endo-(4-Chlorophenyl)-5'-morpholino-spiro[bicyclo[2.2.1]-heptane-2,2'-5-exo-pyrroline] hydriodide By purification, by column chromatography, of the ethanolic mother liquor from methyl β-[3-exo-(4-chlorophenyl)-2-endo-nitro-bicyclo[2.2.1]-hept-5-en-2-yl]propionate (obtained according to Example 32 and Example 1a), the stereoisomeric methyl β-[3-endo-(4-chlorophenyl)-2-exo-nitro-bicyclo[2.2.1]-hept-5-en-2-yl]-propionate can be obtained, by concentration, as a colorless oil (silica gel, eluting agent: methylene chloride).

Completely analogously to the 3-exo-(4-chlorophenyl)-5'-morpholino-spiro[bicyclo[2.2.1]-heptane-2,2'-5-endo-pyrroline] compound, the corresponding stereoisomeric endo-aryl-exo-pyrroline amidine hydriodide can be prepared therefrom in the form of colorless crystals, recrystallized from ethanol, of melting point 279° C. (decomposition).

EXAMPLE 83

(−)-3-exo-(4-Chlorophenyl)-5'-morpholino-spiro[bicyclo[2.2.1]-heptane-2,2'-5-endo-pyrroline] D-hydrogen tartrate The (±)-3-exo-(4-chlorophenyl)-5'-morpholino-spiro[bicyclo[2.2.1]-heptane-2,2'-5-endo-pyrroline] hydriodide obtained, from ethanol, according to Example 32 is converted into the free base with 2 N potassium hydroxide solution/methylene chloride.

12.3 g of the free base (light yellow oil) are dissolved in 400 ml of methanol, and 5.8 g of D(−)-tartaric acid in 200 ml of water are slowly added, whilst stirring. After 2 hours, the fine precipitate is filtered off. The solid is recrystallized from 500 ml of aqueous methanol (1:1). Colorless flakes which decompose at 270° C. are obtained. $[\alpha]_{22}^D = -106°$ (methanol/$H_2O = 3:1$).

Optical rotation of the free base: $[\alpha]_{22}^D = -126°$ (methanol/$H_2O = 3:1$).

The following compound was obtained in a similar manner with modification of the above resolution process: (+)-3-exo-(4-Chlorophenyl)-5'-morpholino-spiro[bicyclo[2.2.1]-heptane-2,2'-5-endo-pyrroline] L-hydrogen tartrate, colorless flakes of decomposition point 270° C., $[\alpha]_{22}^D = +106°$ (methanol/$H_2O = 3:1$).

EXAMPLE 84

(−)-3-exo-(4-Chlorophenyl)-5'-(2,6-dimethylmorpholino)spiro[bicyclo[2.2.1]-heptane-2,2'-5-endo-pyrroline] D-hydrogen tartrate The hydriodide product described in Example 65 is treated with 2 N potassium hydroxide solution and methylene chloride and the organic phase is dried over $Na_2SO_4$, filtered and concentrated. 2.5 g of the oil obtained are dissolved in 100 ml of methanol, and 1 g of D(−)-tartaric acid in 10 ml of water are slowly added. After leaving the mixture to stand overnight, the crystals are filtered off and recrystallized from aqueous methanol (1:1). Colorless crystals of decomposition point 270° C. and $[\alpha]_D^{22} = -107°$ (methanol/water = 3:1) are obtained.

EXAMPLE 85

(−)-3-exo-(4-Fluorophenyl)-5'-morpholino-spiro[bicyclo[2.2.1]-heptane-2,2'-5-endo-pyrroline] D-hydrogen tartrate The D,L-3-exo-(4-fluorophenyl)-5'-morpholino-spiro[bicyclo[2.2.1]-heptane-2,2'-5-endo-pyrroline] hydriodide obtained, from ethanol, according to Example 45 is converted to the salt-free form by extraction by shaking with 2 N potassium hydroxide solution/methylene chloride in the customary manner. The oil (10.7 g) obtained after drying, filtering and evaporating the organic phase is dissolved in 185 ml of methanol, and 4.9 g of D(−)-tartaric acid in 60 ml of water are slowly added, whilst stirring. After subsequently stirring the mixture for 2 hours, the solid is filtered off and recrystallized from aqueous methanol (1:1). Colorless crystals of melting point 256° C. (decomposition) and $[\alpha]_D^{22} = -76°$ (methanol/water=3:1) are obtained.

(+)-3-exo-(4-Fluorophenyl)-5'-morpholino-spiro[bicyclo[2.2.1]-heptane-2,2'-5-endo-pyrroline]L-hydrogen tartrate is obtained in an analogous manner with modification of the above resolution of the racemate. Colorless flakes of decomposition point 255° C. and $[\alpha]_D^{22} = -69°$ (methanol/water=3:1) are obtained.

EXAMPLE 86

(−)-3-exo-(3,4-Dichlorophenyl)-5'-morpholino-spiro[bicyclo[2.2.1]-heptane-2,2'-5-endo-pyrroline] D-hydrogen tartrate The (±)-exo-(3,4-dichlorophenyl)-5'-morpholino-spiro[bicyclo[2.2.1]-heptane-2,2'-5-endo-pyrroline] hydriodide obtained, from ethanol, according to Example 48 is first converted into the salt-free form analogously to Example 83, and is subjected to a racemate resolution with D-tartaric acid. Colorless crystals of melting point 236° C. (decomposition) and $[\alpha]_D^{22} = -101°$ (methanol/water=3:1) are obtained.

We claim:

1. Heterocyclic, spiro-linked amidines of the formula I

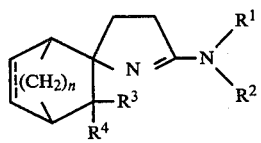

in which (a) n is 1 or 2; (b) $R^1$ and $R^2$ are hydrogen or alkyl radicals which, together with the nitrogen atom, can form a 5-, 6- or 7-membered ring which can be substituted by $C_1$-$C_3$-alkyl, $C_1$-$C_2$-alkoxy, hydroxyl or $C_1$-$C_4$-alkoxycarbonyl groups and in which one of the carbon atoms can also be replaced by an oxygen, sulfur or nitrogen atom, it being possible for the nitrogen atom to be substituted by hydrogen, by the formyl group or by a phenyl radical, which can in turn be monosubstituted or polysubstituted by a $C_1$ to $C_4$-alkyl group or an alkoxy, methylenedioxy, hydroxyl, halogen, nitro or amino group, or it being possible for the nitrogen atom to be substituted by a $C_1$-$C_4$-alkyl group, or in which $R^1$ represents hydrogen and $R^2$ represents a $C_5$-$C_8$-cycloalkyl radical which can be substituted by $C_1$-$C_4$-dialkylamino groups; (c) $R^3$ is hydrogen or methyl and (d) $R^4$ denotes a phenyl radical which is optionally monosubstituted or polysubstituted by $C_1$-$C_4$-alkyl, $C_1$-$C_4$-alkoxy, methylenedioxy, hydroxyl, halogen, cyano, nitro, trifluoromethyl, amino, $C_2$-$C_5$-acylamino or mono- or di-$C_1$-$C_4$-alkylamino groups, or a thiophene radical, and the physiologically acceptable salts of compounds of the formula I.

2. Stereoisomeric exo-aryl-endo-pyrroline amidines as claimed in claim 1, of the general formula XII

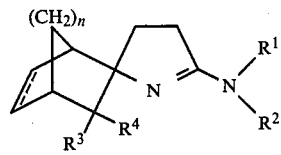

in which $R^1$, $R^2$, $R^3$, $R^4$ and n have the meaning given for claim 1, and their physiologically acceptable salts.

3. Stereoisomeric endo-aryl-exo-pyrroline amidines as claimed in claim 1, of the general formula XVII

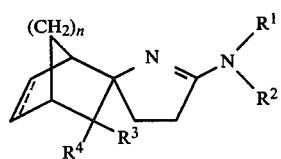

in which $R^1$, $R^2$, $R^3$, $R^4$ and n have the meaning given for claim 1, and their physiologically acceptable salts.

4. Optical isomers of the formula XII and XVII as claimed in claims 2 and 3, and their physiologically acceptable salts.

5. Laevo-rotatory enantiomers of the optical isomers as claimed in claim 4, and their physiologically acceptable salts.

6. The compound of claim 1 which is 3-(4-chlorophenyl)-5'-morpholino-spiro(bicyclo(2,2,1)-heptane-2,2'-5-pyrroline) or a salt thereof.

7. The compound of claim 1 which is 3-(4-fluorophenyl)-5'-morpholino-spiro(bicyclo(2,2,1)-heptane-2,2'-5-pyrroline) or a salt thereof.

8. The compound of claim 1 which is 3-(3,4-dichlorophenyl)-5-morpholino-spiro(bicyclo(2,2,1)-heptane-2,2'-5-pyrroline) or a salt thereof.

9. Antidepressant composition comprising an effective amount of a compound as defined in claim 1 and a physiologically acceptable auxiliary agent or carrier therefor.

10. A method of treating a human patient having depressions which comprises oral administration to said patient of an effective dosage of from about 20 to 120 mg/day of a compound as defined in claim 1.

* * * * *